United States Patent
Mori et al.

(10) Patent No.: US 9,655,826 B2
(45) Date of Patent: May 23, 2017

(54) HAIR DYE COMPOSITION

(71) Applicant: HOYU CO., LTD., Nagoya-shi (JP)

(72) Inventors: Emi Mori, Nagakute (JP); Yoshiyuki Uesawa, Nagakute (JP); Mikinobu Hasegawa, Nagakute (JP); Yoshihito Fuma, Nagakute (JP)

(73) Assignee: HOYU CO., LTD., Nagoya-Shi (JP)

( * ) Notice: Subject to any disclaimer, the term of this patent is extended or adjusted under 35 U.S.C. 154(b) by 0 days.

(21) Appl. No.: 14/907,052

(22) PCT Filed: Jul. 23, 2014

(86) PCT No.: PCT/JP2014/069491
§ 371 (c)(1),
(2) Date: Jan. 22, 2016

(87) PCT Pub. No.: WO2015/016115
PCT Pub. Date: Feb. 5, 2015

(65) Prior Publication Data
US 2016/0158130 A1 Jun. 9, 2016

(30) Foreign Application Priority Data
Jul. 30, 2013 (JP) .................................. 2013-157813

(51) Int. Cl.
A61Q 5/10 (2006.01)
A61K 8/41 (2006.01)
A61K 8/35 (2006.01)

(52) U.S. Cl.
CPC ................ A61K 8/418 (2013.01); A61K 8/35 (2013.01); A61K 8/411 (2013.01); A61K 8/416 (2013.01); A61Q 5/10 (2013.01); A61K 2800/432 (2013.01)

(58) Field of Classification Search
CPC .......... A61Q 5/10; A61Q 5/065; A61K 8/342; A61K 8/34
USPC ........................................................ 8/405
See application file for complete search history.

(56) References Cited

U.S. PATENT DOCUMENTS

| 6,364,913 | B1 | 4/2002 | Hurschmann | |
| 2003/0196280 | A1* | 10/2003 | Lim | A61K 8/411 8/405 |
| 2004/0045101 | A1 | 3/2004 | Miczewski et al. | |
| 2006/0117496 | A1 | 6/2006 | Bolton et al. | |
| 2007/0000070 | A1 | 1/2007 | Vena et al. | |
| 2008/0120791 | A1* | 5/2008 | Hoffmann | A61K 8/11 8/425 |

FOREIGN PATENT DOCUMENTS

| JP | 2000510131 A | 8/2000 |
| JP | 2008521833 A | 6/2008 |
| JP | 2010105998 A | 5/2010 |

OTHER PUBLICATIONS

Clairol "Clairol Loving Care Creme Colourant", Mintel GNPD, online, Oct. 8, 2014, http://www.gnpd.com.
International Search Report in related PCT/JP2014/069491 dated Oct. 28, 2014.
Laboratoires Phytoslba "Color by PhytoSpecific Emulsion Color", Mintel GNPD, online, Oct. 8, 2014, http://www.gnpd.com.
Phitoteraphia Biofitogenia Laboratorial Biota "Embelleze Maxton Hair Colourant Kit", Mintel GNPD, online, Oct. 8, 2014, http://www.gnpd.com.
Strength of Nature "Profectiv Replax & Refresh Relaxer Plus Color" Mintel GNPD, online, Oct. 8, 2014, http://www.gnpd.com.
International Preliminary Search Report on Patentability; International Application No. PCT/JP2014/069491; International Filing Date Jul. 23, 2014; Date of Mailing Feb. 2, 2016, 6 pages.

* cited by examiner

Primary Examiner — Eisa Elhilo
(74) Attorney, Agent, or Firm — Cantor Colburn LLP

(57) ABSTRACT

A hair dye composition is characterized by containing (A) HC BLUE No. 2, (B) DISPERSE VIOLET 1, and (C) at least one of HC YELLOW No. 2 and HC YELLOW No. 4 and has a pH of 7-11. The mass ratio of the content of (A) HC BLUE No. 2 to the content of (B) DISPERSE VIOLET 1 is preferably 1 to 30. The hair dye composition preferably further contains (D) DISPERSE BLACK 9.

3 Claims, No Drawings

HAIR DYE COMPOSITION

BACKGROUND OF THE INVENTION

The present invention relates to a hair dye composition that contains a direct dye and is excellent in the color in hair dyeing and the color after fading.

Generally, there is known a hair dye composition that contains a direct dye as a dye and is used as a semi-permanent hair dye. There is also known an oxidation hair dye as a permanent hair dye in which an oxidation dye permeates the inner part of the cuticle of hair by the action of an alkali agent, and decomposition of a melanin pigment and coloring of a dye are performed using an oxidizing agent. With the hair dye composition containing a direct dye, hair is dyed by the adherence of the direct dye to the keratin in the vicinity of the surface of hair. Therefore, a semi-permanent hair dye can more easily express the color of hair than a permanent hair dye.

However, it is generally known that the degree of fading of a direct dye is larger than that of a permanent hair dye. Further, there is a case where the degree of fading is larger depending on the type or the combination of direct dyes. Therefore, there is a case where the color after fading is greatly different from the color in hair dyeing, depending on the type or the combination of direct dyes.

In this regard, a hair dye composition disclosed in Patent Document 1 has been known, which contains a specific nonionic surfactant and a water-soluble polymer in combination. Thereby, in the hair dye composition of Patent Document 1, the hair dyeing ability is improved to reduce the change of color due to fading.

PRIOR ART DOCUMENTS

Patent Documents

Patent Document 1: Japanese Laid-Open Patent Publication No. 2010-105998

SUMMARY OF THE INVENTION

However, the hair dye composition of Patent Document 1 has a problem that, particularly when the color in hair dyeing is brown to black, the suppression of color change after fading is insufficient. For example, there is a problem that, when the color in hair dyeing is brown to black, greenish color may develop after fading depending on the type or the combination of direct dyes.

As a result of intensive and extensive researches by the present inventors, the present invention has been made based on the findings that, in the hair dye composition containing a direct dye, the color in hair dyeing and the color after fading can be improved by using specific direct dyes in combination. An objective of the present invention is to provide a hair dye composition that is excellent in the color in hair dyeing and the color after fading.

To achieve the foregoing objective and in accordance with one aspect of the present invention, a hair dye composition of the present invention is characterized by containing: (A) HC BLUE No. 2; (B) DISPERSE VIOLET 1; and (C) at least one of HC YELLOW No. 2 and HC YELLOW No. 4. The composition has a pH of 7 to 11. The mass ratio of the content of (A) HC BLUE No. 2 to the content of (B) DISPERSE VIOLET 1 is preferably 1 to 30. The hair dye composition preferably contains (D) DISPERSE BLACK 9. The name of each component is based on the International Nomenclature of Cosmetic Ingredients.

According to the hair dye composition of the present invention, the color in hair dyeing and the color after fading are improved.

DETAILED DESCRIPTION OF THE PREFERRED EMBODIMENTS

A hair dye composition according to one embodiment of the present invention will now be described.

The hair dye composition of the present embodiment contains (A) HC BLUE No. 2, (B) DISPERSE VIOLET 1, and (C) at least one of HC YELLOW No. 2 and HC YELLOW No. 4. The composition preferably further contains (D) DISPERSE BLACK 9 and a solvent.

(A) HC BLUE No. 2 (2,2'-[[4-[(2-hydroxyethyl)amino]-3-nitrophenyl]imino]bisethanol) is a kind of nitro dye, and it is blended in to facilitate the expression of brown to black color. Further, (A) HC BLUE No. 2 is blended in particularly to improve the color in hair dyeing. The content of (A) HC BLUE No. 2 in the hair dye composition is preferably 0.1% by mass or more, more preferably 0.5% by mass or more, further preferably 1% by mass or more. The expression of brown to black color is facilitated as the content of (A) HC BLUE No. 2 increases.

Further, the content of (A) HC BLUE No. 2 in the hair dye composition is preferably 3% by mass or less, more preferably 2.5% by mass or less, further preferably 2% by mass or less. By setting the content of (A) HC BLUE No. 2 to 3% by mass or less, the development of purplish color can be further suppressed, for example, when brown to black color is expressed in hair dyeing. Further, the solubility of a dye in a solvent can be further improved.

(B) DISPERSE VIOLET 1 (1,4-diaminoanthraquinone) is a kind of disperse dye, and it is blended in to facilitate the expression of brown to black color. Further, (B) DISPERSE VIOLET 1 is blended in not only to improve the color in hair dyeing but also to further suppress the change of color after fading. The content of (B) DISPERSE VIOLET 1 in the hair dye composition is preferably 0.05% by mass or more, more preferably 0.1% by mass or more, further preferably 0.3% by mass or more. The expression of brown to black color is facilitated as the content of (B) DISPERSE VIOLET 1 increases.

Further, the content of (B) DISPERSE VIOLET 1 in the hair dye composition is preferably 1.5% by mass or less, more preferably 1% by mass or less, further preferably 0.8% by mass or less. By setting the content of (B) DISPERSE VIOLET 1 to 1.5% by mass or less, the development of purplish color can be further suppressed when brown to black color is expressed in hair dyeing.

(C) HC YELLOW No. 2 (N-(2-hydroxyethyl)-2-nitroaniline) and HC YELLOW No. 4 (2-[[2-(2-hydroxyethoxy)-4-nitrophenyl]amino]ethanol) are a kind of nitro dye, and they are blended in to facilitate the expression of brown to black color. With respect to these components (C), only one of them may be singly contained, or two of them may be contained in combination. Further, the component (C) is blended in not only to improve the color in hair dyeing but also to further suppress the change of color after fading. The content of the component (C) in the hair dye composition is preferably 0.2% by mass or more, more preferably 0.4% by mass or more. As the content of the component (C) increases, the development of purplish color can be further suppressed when brown to black color is expressed in hair dyeing.

Further, the content of the component (C) in the hair dye composition is preferably 0.8% by mass or less, more preferably 0.6% by mass or less. The expression of brown to black color is facilitated by setting the content of the component (C) to 0.8% by mass or less.

(D) DISPERSE BLACK 9 (2,2'-[[4-[(4-aminophenyl)azo]phenyl]imino]bisethanol) is a kind of disperse dye, and it is preferably blended in to further suppress the change of color after fading. The content of (D) DISPERSE BLACK 9 in the hair dye composition is preferably 0.05% by mass or more, more preferably 0.1% by mass or more. The development of greenish color after fading can be further suppressed as the content of (D) DISPERSE BLACK 9 increases.

Further, the content of (D) DISPERSE BLACK 9 in the hair dye composition is preferably 0.5% by mass or less, more preferably 0.2% by mass or less. The development of orange color after fading can be further suppressed by setting the content of (D) DISPERSE BLACK 9 to 0.5% by mass or less.

The mass ratio of the content of (A) HC BLUE No. 2 to the content of (B) DISPERSE VIOLET 1 in the hair dye composition is preferably 1 or more. As the mass ratio increases, the development of purplish color can be further suppressed when brown to black color is expressed in hair dyeing.

Further, the mass ratio of the content of (A) HC BLUE No. 2 to the content of (B) DISPERSE VIOLET 1 in the hair dye composition is preferably 30 or less. The color in hair dyeing can be improved by setting the mass ratio to 30 or less.

Examples of solvents include water and organic solvents. Examples of organic solvents include ethanol, isopropanol, benzyl alcohol, benzyloxy ethanol, glycol, and glycerin. Examples of glycol include ethylene glycol, diethylene glycol, triethylene glycol, polyethylene glycol, propylene glycol, dipropylene glycol, isoprene glycol, and 1,3-butylene glycol. Examples of glycerin include glycerin, diglycerin, and polyglycerin. Among specific examples of these solvents, only one of them may be singly contained, or two of them may be contained in combination.

The content of the organic solvent in the hair dye composition is preferably 0.1% by mass or more, more preferably 1% by mass or more, further preferably 5% by mass or more. The hair dyeing ability further improves as the content increases. Further, the content of the organic solvent in the hair dye composition is preferably 25% by mass or less, more preferably 20% by mass or less, further preferably 10% by mass or less. The reduction in hair dyeing ability can be further prevented by setting the content to 25% by mass or less.

The pH of the hair dye composition in the present embodiment is 7 or more, preferably 8 or more. The color in hair dyeing and the color after fading can be improved by setting the pH to 7 or more. Further, dye stability can be further improved. On the other hand, the pH of the hair dye composition in the present embodiment is 11 or less, preferably 10 or less. The color in hair dyeing and the color after fading can be improved by setting the pH to 11 or less. Further, the stimulation to a scalp can be further reduced. The pH of the hair dye composition in the present embodiment can be adjusted using a pH adjuster. Examples of pH adjusters include an organic acid and an alkali agent. Examples of organic acids include lactic acid, levulinic acid, glycolic acid, tartaric acid, malic acid, pyrrolidone carboxylic acid (PCA), succinic acid, citric acid, and glutamic acid. Examples of alkali agents include ammonia, alkanolamine, organic amines, inorganic alkali, basic amino acid, and salts thereof. Examples of alkanolamine include monoethanolamine and triethanolamine. Examples of organic amines include 2-amino-2-methyl-1,3-propanediol, and guanidine. Examples of inorganic alkali include sodium hydroxide, potassium hydroxide, sodium carbonate, and potassium carbonate. Examples of basic amino acids include arginine and lysine. Examples of the salts include an ammonium salt. Among the specific examples of these pH adjusters, only one of them may be singly contained, or two of them may be contained in combination.

The hair dye composition of the present embodiment may contain other components that are generally contained in a hair dye composition and do not inhibit the action of the components described above and the advantage of the present invention. Examples of such components include higher alcohols, surfactants, oily components, polymer compounds, direct dyes other than the above, sugar, preservatives, chelating agents, stabilizers, herbal extract, vitamin, perfume, antioxidants, ultraviolet absorbers, and inorganic salts. With respect to these components, only one of the specific examples thereof may be singly contained, or two of them may be contained in combination.

Examples of higher alcohols include lauryl alcohol, myristyl alcohol, cetyl alcohol (cetanol), 2-hexyldecanol, cetostearyl alcohol, stearyl alcohol, isostearyl alcohol, oleyl alcohol, arachyl alcohol, 2-octyldodecanol, behenyl alcohol, decyltetradecanol, and lanolin alcohol.

The surfactants can be blended in as a solubilizing agent that solubilizes each component. Further, they can be blended in to adjust the viscosity of the composition or to improve the viscosity stability thereof. Examples of surfactants include nonionic surfactants, cationic surfactants, anionic surfactants, and amphoteric surfactants.

Examples of nonionic surfactants include polyoxyalkylene-polyoxypropylene alkyl ethers, alkylene sorbitan fatty acid esters, alkylene alkyl glycol fatty acid esters, polyoxyalkylene fatty acid amides, aliphatic alkanol amides, and alkyl glucosides.

Examples of polyoxyalkylene-polyoxypropylene alkyl ethers include polyoxyethylene (hereinafter, referred to as POE) cetyl ether, POE stearyl ether (steareth), POE behenyl ether, POE oleyl ether, POE lauryl ether, POE octyldodecyl ether, POE hexyldecyl ether, POE isostearyl ether, POE nonylphenyl ether, and POE octylphenyl ether.

Examples of alkylene sorbitan fatty acid esters and alkylene alkyl glycol fatty acid esters include POE sorbitan monooleate, POE sorbitan monostearate, POE sorbitan monopalmitate, POE sorbitan monolaurate, POE sorbitan trioleate, POE glyceryl monostearate, POE glyceryl monomyristate, POE sorbitol tetraoleate, POE sorbitol hexastearate, POE sorbitol monolaurate, POE sorbitol yellow bees wax, polyethylene glycol monooleate, polyethylene glycol monostearate, polyethylene glycol monolaurate, lipophilic glyceryl monooleate, lipophilic glyceryl monostearate, self-emulsifying glyceryl monostearate, sorbitan monooleate, sorbitan sesquioleate, sorbitan trioleate, sorbitan monostearate, sorbitan monopalmitate, sorbitan monolaurate, sucrose fatty acid ester, decaglyceryl monolaurate, decaglyceryl monostearate, decaglyceryl monooleate, and decaglyceryl monomyristate.

Examples of polyoxyalkylene fatty acid amides and aliphatic alkanol amides include POE lauric acid monoethanolamide, POE coconut oil fatty acid monoethanolamide, and polyoxypropylene myristic acid monoethanolamide.

Examples of alkyl glucosides include a C8-16 alkyl glucoside, polyoxyethylene methyl glucoside, and polyoxyethylene dioleic acid methyl glucoside.

Examples of cationic surfactants include lauryl trimethylammonium chloride, cetyltrimethylammonium chloride, stearyltrimethylammonium chloride, alkyltrimethylammonium chloride, distearyldimethylammonium chloride, cetyltrimethylammonium bromide, stearyltrimethylammonium bromide, lanolin fatty acid aminopropylethyldimethylammonium ethyl sulfate, stearyltrimethylammonium saccharin, cetyltrimethylammonium saccharin, methacryloyloxyethyltrimethylammonium chloride, and behenyltrimethylammonium methyl sulfate.

Examples of anionic surfactants include an alkylsulfate ester salt such as sodium lauryl sulfate and triethanolamine lauryl sulfate, an alkyl ether sulfate ester salt such as sodium POE lauryl ether sulfate, sodium stearoylmethyltaurine, triethanolamine dodecylbenzenesulfonate, sodium tetradecene sulfonate, a C6-24 alkyl ether carboxylic acid, a C6-24 hydroxyalkyl ether carboxylic acid, a polyoxyalkylenated C6-24 alkyl ether carboxylic acid, a polyoxyalkylenated C6-24 alkyl aryl ether carboxylic acid, a polyoxyalkylenated C6-24 alkyl amide ether carboxylic acid, and alkali metal salts thereof (such as sodium salt and potassium salt), an organic amine salt (such as monoethanolamine salt, diethanolamine salt, triethanolamine salt, and monoisopropanolamine salt), POE lauryl ether phosphoric acid and a salt thereof, N-lauroyl glutamates, and N-lauroyl methyl-β-alanine salts.

Examples of amphoteric surfactants include sodium lauroamphoacetate and sodium cocoamphoacetate. Among the specific examples of these surfactants, only one of them may be singly contained, or two of them may be contained in combination.

Examples of oily components include oils and fats, wax, hydrocarbon, higher fatty acid, alkyl glyceryl ether, ester, and silicone.

Specific examples of oils and fats include olive oil, camellia oil, shea fat, almond oil, safflower oil, sunflower oil, soybean oil, cottonseed oil, sesame oil, corn oil, rapeseed oil, rice bran oil, rice germ oil, grape seed oil, avocado oil, macadamia nut oil, castor oil, coconut oil, and evening primrose oil. Specific examples of wax include yellow bees wax, candelilla wax, carnauba wax, jojoba oil, and lanolin.

Specific examples of hydrocarbons include paraffin, olefin oligomer, polyisobutene, hydrogenated polyisobutene, mineral oil, squalane, polybutene, polyethylene, microcrystallin wax, and vaseline. Specific examples of higher fatty acid include lauric acid, myristic acid, palmitic acid, stearic acid, behenic acid, isostearic acid, 12-hydroxystearic acid, oleic acid, and lanolin fatty acid. Specific examples of alkyl glyceryl ether include batyl alcohol, chimyl alcohol, selachyl alcohol, and isostearyl glyceryl ether.

Specific examples of esters include diisopropyl adipate, isopropyl myristate, cetyl octanoate, isononyl isononanoate, octyldodecyl myristate, isopropyl palmitate, stearyl stearate, myristyl myristate, isotridecyl myristate, 2-ethylhexyl palmitate, octyldodecyl ricinoleate, C10-30 cholesterol/lanosterol esters, cetyl lactate, lanolin acetate, ethylene glycol di-2-ethylhexanoate, pentaerythritol fatty acid ester, dipentaerythritol fatty acid ester, cetyl caprate, glyceryl tricaprylate, diisostearyl malate, dioctyl succinate, diethoxyethyl succinate, and cetyl 2-ethylhexanoate.

Specific examples of silicones include dimethylpolysiloxane (dimethicone), methylphenylpolysiloxane, decamethylcyclopentasiloxane, dodecamethylcyclohexasiloxane, a terminal hydroxyl group-modified dimethylpolysiloxane (dimeticonol), highly polymerized silicone having an average degree of polymerization of 650 to 10000, polyether-modified silicone (for example, (PEG/PPG/butylene/dimethicone) copolymer), amino-modified silicone, betaine-modified silicone, alkyl-modified silicone, alkoxy-modified silicone, mercapto-modified silicone, carboxy-modified silicone, and fluorine-modified silicone. Among the specific examples of these oily components, only one of them may be singly contained, or two of them may be contained in combination.

Examples of polymer compounds include nonionic polymers, anionic polymers, cationic polymers, and amphoteric polymers.

Examples of nonionic polymers include hydroxyethylcellulose, hydroxypropylmethylcellulose, hydroxypropylcellulose, methylcellulose, dextrin, galactan, pullulan, highly polymerized polyethylene glycol, polyvinyl alcohol, a homo- and co-polymer of vinylpyrrolidone, particularly, a polyvinyl pyrrolidone homopolymer, a copolymer of vinylpyrrolidone and vinyl acetate, trade name "Luviskol" (manufactured by BASF A.G.), and a terpolymer of vinylpyrrolidone, vinyl acetate, and vinyl propionate. Examples of nonionic polymers further include various copolymers of acrylate, methacrylate, acrylamide, and methacrylamide, such as polyacrylamide having a molecular weight of 100,000 or more, and a dimethylhydantoin-formaldehyde resin.

Examples of anionic polymers include xanthan gum, carrageenan, sodium alginate, gum arabic, pectin, and a carboxyvinyl polymer.

Examples of cationic polymers include cationized cellulose such as O-[2-hydroxy-3-(trimethylammonio)propyl]hydroxyethylcellulose chloride, O-[2-hydroxy-3-(lauryldimethylammonio)propyl]hydroxyethylcellulose chloride, and hydroxyethylcellulose-dimethyldiallylammonium chloride; cationized guar gum such as [O-[2-hydroxy-3-(trimethylammonio)propyl]guar gum chloride; cationized polysaccharide obtained by cationizing polysaccharide such as cellulose derivatives, natural gum, starch, and dextran, such as cationized dextran such as dextran hydroxypropyl trimethylammonium ether chloride; cationized hydrolyzed protein obtained by cationizing hydrolyzed protein such as [N-[2-hydroxy-3-(trimethylammonio)propyl]hydrolyzed collagen chloride, [N-[2-hydroxy-3-(trimethylammonio)propyl]hydrolyzed silk chloride, [N-[2-hydroxy-3-(trimethylammonio)propyl]hydrolyzed keratin chloride, [N-[2-hydroxy-3-(trimethylammonio)propyl]hydrolyzed conchiolin chloride, [N-[2-hydroxy-3-(stearyldimethylammonio)propyl]hydrolyzed keratin chloride, [N-[2-hydroxy-3-(stearyldimethylammonio)propyl]hydrolyzed collagen chloride, [N-[2-hydroxy-3-(stearyldimethylammonio)propyl] hydrolyzed silk chloride, [N-[2-hydroxy-3-(stearyldimethylammonio)propyl]hydrolyzed conchiolin chloride, [N-[2-hydroxy-3-(lauryldimethylammonio)propyl]hydrolyzed keratin chloride, [N-[2-hydroxy-3-(lauryldimethylammonio)propyl]hydrolyzed collagen chloride, [N-[2-hydroxy-3-(lauryldimethylammonio)propyl]hydrolyzed silk chloride, [N-[2-hydroxy-3-(lauryldimethylammonio)propyl]hydrolyzed conchiolin chloride, [N-[2-hydroxy-3-(coconut oil alkyldimethylammonio)propyl] hydrolyzed soy protein chloride, [N-[2-hydroxy-3-(coconut oil alkyldimethylammonio)propyl]hydrolyzed collagen chloride, [N-[2-hydroxy-3-(coconut oil alkyldimethylammonio)propyl]hydrolyzed silk chloride, [N-[2-hydroxy-3-(coconut oil alkyldimethylammonio)propyl]hydrolyzed keratin chloride, and [N-[2-hydroxy-3-(coconut oil alkyldimethylammonio)propyl]hydrolyzed conchiolin chloride;

cationized vinyl or acrylic polymers such as dimethyldiallylammonium chloride/acrylamide copolymer, β-methacryloxyethyltrimethylammonium/acrylamide copolymer, vinylpyrrolidone/N,N-dimethylaminoethyl methacrylate copolymer diethyl sulfate salt, β-methacryloxyethyltrimethylammonium/acrylamide copolymer, and poly(dimethylmethylene piperidinium)chloride; polyglycol polyamine condensation products such as N,N-dimethylaminoethyl methacrylate diethyl sulfate salt/N,N-dimethylacrylamide/polyethylene glycol dimethacrylate; dimethyl adipionate/aminohydroxypropyl diethyltriamine copolymer; and aminoethylaminopropyl/methylpolysiloxane copolymer.

Examples of amphoteric polymers include an N-methacryloylethyl-N,N-dimethylammonium-α-N-methylcarboxybetaine/butyl methacrylate copolymer (trade name; YUKAFORMER AM-75; manufactured by Mitsubishi Chemical Corporation), a hydroxypropyl acrylate/butylaminoethyl methacrylate/octylamide acrylate copolymer (trade name; AMPHOMER 28-4910; manufactured by National Starch & Chemical Company), a dimethyldiallylammonium chloride/acrylic acid copolymer (trade name; Merquat 280, 295; manufactured by Ondeo Nalco Company), a terpolymer of dimethyldiallylammonium chloride/acrylamide/acrylic acid (trade name; Merquat PLUS 3330, 3331; manufactured by Ondeo Nalco Company), and an acrylic acid/methyl acrylate/methacrylamidepropyltrimethylammonium chloride copolymer (trade name; Merquat 2001; manufactured by Ondeo Nalco Company). Among specific examples of these polymer compounds, only one of them may be singly contained, or two of them may be contained in combination.

Examples of sugar include sorbitol, maltose, glycosyl trehalose, and N-acetyl glucosamine. Examples of preservatives include para-hydroxybenzonate, paraben, methylparaben, and sodium benzoate. Examples of chelating agents include edetic acid (ethylenediaminetetraacetic acid (EDTA)) and salts thereof, diethylenetriamine pentaacetic acid and salts thereof, and hydroxyethanediphosphonic acid (etidronic acid, HEDP) and salts thereof.

Examples of stabilizers include phenacetin, 8-hydroxyquinoline, acetanilide, sodium pyrophosphate, barbituric acid, uric acid, and tannic acid. Examples of antioxidants include ascorbic acid and sulfites. Examples of inorganic salts include sodium chloride and sodium carbonate.

Examples of direct dyes other than the above include acid dyes, nitro dyes, basic dyes (cationic dyes), and disperse dyes. These dyes may be blended in with the hair dye composition within the range that does not impair the object or advantages of the present invention.

Examples of acid dyes include Red No. 2, Red No. 3, Red No. 102, Red No. 104-(1), Red No. 105-(1), Red No. 106, Red No. 201, Red No. 227, Red No. 230-(1), Red No. 230-(2), Red No. 231, Red No. 232, Red No. 401, Red No. 502, Red No. 503, Red No. 504, Red No. 506, Yellow No. 4, Yellow No. 5, Yellow No. 202-(1), Yellow No. 202-(2), Yellow No. 203, Yellow No. 402, Yellow No. 403-(1), Yellow No. 406, Yellow No. 407, Orange No. 205, Orange No. 207, Orange No. 402, Green No. 3, Green No. 204, Green No. 205, Green No. 401, Green No. 402, Violet No. 401, Blue No. 1, Blue No. 2, Blue No. 202, Blue No. 203, Blue No. 205, Brown No. 201, Black No. 401, Acid Blue 1, Acid Blue 3, Acid Blue 62, Acid Black 52, Acid Brown 13, Acid Green 50, Acid Orange 6, Acid Red 14, Acid Red 35, Acid Red 73, Acid Red 184, and Brilliant Black 1.

Examples of nitro dyes include 4-nitro-o-phenylenediamine, 2-nitro-p-phenylenediamine, 2-amino-4-nitrophenol, 2-amino-5-nitrophenol, picramic acid, picric acid, and salts thereof, HC Blue No. 4, HC Blue No. 5, HC Blue No. 6, HC Blue No. 8, HC Blue No. 9, HC Blue No. 10, HC Blue No. 11, HC Blue No. 12, HC Blue No. 13, HC Blue No. 14, HC Brown No. 1, HC Brown No. 2, HC Green No. 1, HC Orange No. 1, HC Orange No. 2, HC Orange No. 3, HC Orange No. 5, HC Red No. 1, HC Red No. 3, HC Red No. 7, HC Red No. 8, HC Red No. 9, HC Red No. 10, HC Red No. 11, HC Red No. 13, HC Red No. 14, HC Violet No. 1, HC Violet No. 2, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, and HC Yellow No. 15.

Examples of basic dyes include Red No. 213, Red No. 214, Basic Blue 3, Basic Blue 6, Basic Blue 7, Basic Blue 9, Basic Blue 26, Basic Blue 41, Basic Blue 99, Basic Brown 4, Basic Brown 16, Basic Brown 17, Basic Brown 1, Basic Brown 4, Basic Orange 1, Basic Orange 2, Basic Red 1, Basic Red 2, Basic Red 22, Basic Red 46, Basic Red 76, Basic Red 118, Basic Violet 1, Basic Violet 3, Basic Violet 4, Basic Violet 10, Basic Violet 11:1, Basic Violet 14, Basic Violet 16, Basic Yellow 11, Basic Yellow 28, and Basic Yellow 57.

Examples of disperse dyes include Disperse Blue 1, Disperse Blue 3, Disperse Blue 7, Disperse Brown 4, Disperse Orange 3, Disperse Red 11, Disperse Red 15, Disperse Red 17, Disperse Violet 4, and Disperse Violet 15.

Examples of direct dyes further include 1-amino-4-methylanthraquinone, 1,4-diaminoanthraquinone, and salts thereof, and direct dyes provided by "Ministerial Ordinance to Provide for Tar Dyes that can be used in Pharmaceuticals and the like" (notified in 1966 by the Ministry of Health and Welfare). These direct dyes may be blended in singly or in combination of two or more.

Examples of the dosage form of the hair dye composition of the present embodiment include, but are not particularly limited to, liquid, gel, foam, and cream dosage form. Examples of liquid dosage form include an aqueous solution, a dispersion, and an emulsion. The container filled with the hair dye composition of the present embodiment is not particularly limited. When the dosage form of the hair dye composition is foam, for example, an aerosol container may be used, or a nonaerosol container may be used. Examples of nonaerosol containers include a pump foamer container and a squeeze foamer container. The method for coating hair with the above hair dye composition is not particularly limited, but a known method can be arbitrarily used. Examples include a coating method using a comb or a brush, a coating method by manual combing, and a coating method by spraying. The method for dyeing hair using the above hair dye composition is not particularly limited, but may be a method for dyeing hair by a set of coating and dyeing operations, or may be applied to a slow dyeing method in which hair is gradually dyed by repeated operations of coating and dyeing.

Next, operation of the hair dye composition of the present embodiment will be described.

The hair dye composition of the present embodiment contains: (A) HC BLUE No. 2; (B) DISPERSE VIOLET 1; and (C) at least one of HC YELLOW No. 2 and HC YELLOW No. 4, wherein the composition has a pH adjusted to 7 to 11. The color in hair dyeing and the color after fading can be improved by the synergistic effect of each component. In particular, when the color in hair dyeing is brown to black, the development of purplish color can be further suppressed. Further, the development of greenish or orange color can be further suppressed after fading.

According to the hair dye composition of the present embodiment, the following advantages are obtained.

(1) The hair dye composition of the present embodiment contains: (A) HC BLUE No. 2; (B) DISPERSE VIOLET 1; and (C) at least one of HC YELLOW No. 2 and HC YELLOW No. 4, wherein the composition has a pH adjusted to 7 to 11. Therefore, the color in hair dyeing and the color after fading is improved.

(2) In the hair dye composition of the present embodiment, the mass ratio of the content of (A) HC BLUE No. 2 to the content of (B) DISPERSE VIOLET 1 is preferably 1 to 30. Therefore, particularly when the color in hair dyeing is brown to black, the development of purplish color is further suppressed.

(3) The hair dye composition of the present embodiment preferably contains (D) DISPERSE BLACK 9. Therefore, particularly when the color in hair dyeing is brown to black, the development of greenish color is further suppressed after fading.

The above embodiment may be changed as follows.

In the above embodiment, the hair dye composition was constituted as a one-pack type composition in which all the components constituting the above hair dye composition were blended in. However, the components may be separated and constituted as plural-type compositions so that the compositions may be mixed immediately before use.

EXAMPLES

Next, the above embodiments will be more specifically described with reference to Examples and Comparative Examples.

Each component shown in Tables 1 and 2 was mixed to prepare a hair dye composition of each Example and Comparative Example. The unit of the numerical values showing the formulation of each component in Tables 1 and 2 is % by mass. Further, the description of "A to D" in the "component" column in the Tables shows a compound corresponding to each component described in the claims of the present invention.

pH Measurement of Hair Dye Composition

Twenty grams of a hair dye composition in each example were weighed into a 30 mL standard bottle to measure the pH of an undiluted solution using a pH meter (Navi h•F-52) manufactured by Horiba, Ltd.

Preparation of Hair-Bundle for Evaluation

One gram of white hair 100% hair (manufactured by Beaulax Co., Ltd.) was coated with 2 g of Dark and Lovely (manufactured by SOFTSHEEN-CARSON Inc.) as a relaxer and treated at 30° C. for 20 minutes. After the treatment, the treated hair was subjected to plain rinse and shampoo twice and hair treatment once using the appended goods of the above product, followed by drying the hair to prepare a hair-bundle for evaluation. The hair-bundle for evaluation was used to evaluate the color in hair dyeing and the color after fading in accordance with the following methods.

<Evaluation of Color in Hair Dyeing>

The hair-bundle for evaluation was immersed in water, dried with a towel, coated with 1.5 g of a hair dye composition of each example prepared according to the above procedure, and dyed at 30° C. for 30 minutes. After the hair dyeing, the hair was subjected to a plain rinse and a hair treatment (manufactured by Hoyu Co., Ltd., Bigen Treatment Rinse) once, followed by drying the hair. Subsequently, the color of the hair-bundle for evaluation was visually evaluated by 20 panelists under a standard light source.

The results were rated as follows: 5 points for "very excellent in color without purplish color", 4 points for "excellent", 3 points for "good", 2 points for "slightly poor", and 1 point for "poor". Then, the average value of the points by 10 panelists was calculated for each example, and the following ratings were given: when the average value was 4.6 points or more, the rating was "5: very excellent"; when the average value was 3.6 points to 4.5 points, the rating was "4: excellent"; when the average value was 2.6 points to 3.5 points, the rating was "3: good"; when the average value was 1.6 points to 2.5 points, the rating was "2: slightly poor"; and when the average value was 1.5 points or less, the rating was "1: not allowable". The results are shown in Tables 1 and 2.

<Evaluation of Color After Fading>

The hair-bundle after hair dyeing of each example prepared according to the above procedure was immersed in 100 ml of a 1% sodium lauryl sulfate aqueous solution at 50° C. for 8 minutes. Subsequently, the hair was subjected to a plain rinse and dried. Thereafter, the color of the hair-bundle for evaluation was visually evaluated by 10 panelists under a standard light source.

The results were rated as follows: 5 points for "very excellent in color without greenish or orange color", 4 points for "excellent", 3 points for "good", 2 points for "slightly poor", and 1 point for "poor". Then, the average value of the points by 10 panelists was calculated for each example, and the following ratings were given: when the average value was 4.6 points or more, the rating was "5: very excellent"; when the average value was 3.6 points to 4.5 points, the rating was "4: excellent"; when the average value was 2.6 points to 3.5 points, the rating was "3: good"; when the average value was 1.6 points to 2.5 points, the rating was "2: slightly poor"; and when the average value was 1.5 points or less, the rating was "1: poor". The results are shown in Tables 1 and 2.

TABLE 1

|  | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|
| Stearyl alcohol | 6 | 6 | 6 | 6 | 6 | 6 | 6 | 6 | 6 | 6 | 6 |
| Steareth-20 | 2 | 2 | 2 | 2 | 2 | 2 | 2 | 2 | 2 | 2 | 2 |
| Glyceryl stearate | 2 | 2 | 2 | 2 | 2 | 2 | 2 | 2 | 2 | 2 | 2 |
| Propylene glycol | 10 | 10 | 10 | 10 | 10 | 10 | 10 | 10 | 10 | 10 | 10 |
| (A) HC BLUE NO. 2 | 0.1 | 0 | 0.1 | 0.1 | 0.8 | 2.1 | 1 | 1.1 | 0.9 | 0.9 | 0.9 |
| (B) DISPERSE VIOLET 1 | 0.6 | 0.05 | 1.5 | 0.6 | 0.8 | 0.08 | 0.2 | 0.1 | 0.6 | 0.6 | 0.6 |
| (C) HC YELLOW NO. 4 | 0.2 | 0.2 | 0.2 | 0.8 | 0.7 | 0.4 | 0.3 | 0.3 | 0.7 | 0.7 | 0.7 |
| (C) HC YELLOW NO 2 |  |  |  |  |  |  |  |  |  |  |  |

TABLE 1-continued

|  | | | | | | | | | | | |
|---|---|---|---|---|---|---|---|---|---|---|---|
| (D) DISPERSE BLACK 9 | | | | | | | | | 0.05 | 0.5 | 0.1 |
| BASIC BLUE 99 | 0.05 | 0.1 | 0.05 | 0.03 | 0.1 | 0.1 | 0.05 | 0.04 | 0.1 | 0.1 | 0.1 |
| Monoethanolamine | q.s. | q.s. | q.s. | q.s. | q.s. | q.s. | q.s. | q.s. | q.s. | q.s. | q.s. |
| Purified water | q.s. | q.s. | q.s. | q.s. | q.s. | q.s. | q.s. | q.s. | q.s. | q.s. | q.s. |
| pH | | | | | | 9-10 | | | | | |
| Total | 100 | 100 | 100 | 100 | 100 | 100 | 100 | 100 | 100 | 100 | 100 |
| Mass ratio (A/B) of the content of component (A) to the content of component (B) | 0.167 | 60 | 0.067 | 0.167 | 1 | 26.25 | 5 | 11.000 | 1.5 | 1.5 | 1.5 |
| Rating | | | | | | | | | | | |
| Color in hair dyeing | 3 | 3 | 3 | 3 | 4 | 4 | 4 | 4 | 4 | 4 | 4 |
| Color after fading | 3 | 3 | 3 | 3 | 3 | 3 | 3 | 3 | 4 | 4 | 5 |

|  |  | Example 12 | Example 13 | Example 14 | Example 15 | Example 16 | Example 17 | Example 18 | Example 19 | Example 20 |
|---|---|---|---|---|---|---|---|---|---|---|
|  | Stearyl alcohol | 6 | 6 | 6 | 6 | 6 | 6 | 6 | 6 | 6 |
|  | Steareth-20 | 2 | 2 | 2 | 2 | 2 | 2 | 2 | 2 | 2 |
|  | Glyceryl stearate | 2 | 2 | 2 | 2 | 2 | 2 | 2 | 2 | 2 |
|  | Propylene glycol | 10 | 10 | 10 | 10 | 10 | 10 | 10 | 10 | 10 |
| (A) | HC BLUE NO. 2 | 0.9 | 1 | 1 | 2 | 0.6 | 1.7 | 0.6 | 1 | 1 |
| (B) | DISPERSE VIOLET 1 | 0.6 | 0.6 | 0.6 | 0.6 | 0.05 | 0.1 | 0.5 | 0.6 | 0.6 |
| (C) | HC YELLOW NO. 4 | 0.7 | 0.7 | | 0.7 | 0.3 | 0.33 | 0.5 | 0.7 | 0.7 |
| (C) | HC YELLOW NO 2 | | | 0.7 | | | | | | |
| (D) | DISPERSE BLACK 9 | 0.2 | 0.2 | 0.2 | 0.2 | 0.2 | 0.2 | 0.2 | 0.2 | 0.2 |
|  | BASIC BLUE 99 | 0.1 | 0.1 | 0.1 | 0.1 | 0 | 0.1 | 0.1 | 0.1 | 0.1 |
|  | Monoethanolamine | q.s. | q.s. | q.s. | q.s. | q.s. | q.s. | q.s. | q.s. | q.s. |
|  | Purified water | q.s. | q.s. | q.s. | q.s. | q.s. | q.s. | q.s. | q.s. | q.s. |
|  | pH | | | | 9-10 | | | | 7 | 11 |
|  | Total | 100 | 100 | 100 | 100 | 100 | 100 | 100 | 100 | 100 |
|  | Mass ratio (A/B) of the content of component (A) to the content of component (B) | 1.5 | 1.667 | 1.667 | 3.333 | 12 | 17.000 | 1.2 | 1.667 | 1.667 |
|  | Rating | | | | | | | | | |
|  | Color in hair dyeing | 4 | 5 | 5 | 5 | 5 | 4 | 4 | 4 | 4 |
|  | Color after fading | 5 | 5 | 5 | 5 | 5 | 5 | 5 | 5 | 5 |

TABLE 2

|  | Comparative Example 1 | Comparative Example 2 | Comparative Example 3 |
|---|---|---|---|
| Stearyl alcohol | 6 | 6 | 6 |
| Steareth-20 | 2 | 2 | 2 |
| Glyceryl stearate | 2 | 2 | 2 |
| Propylene glycol | 10 | 10 | 10 |
| (A) HC BLUE NO. 2 | — | 1 | 1 |
| (B) DISPERSE VIOLET 1 | 0.6 | — | 0.6 |
| (C) HC YELLOW NO. 4 | 0.7 | 0.7 | — |
| (D) DISPERSE BLACK 9 | 0.2 | 0.2 | 0.2 |
| BASIC BLUE 99 | 0.1 | 0.1 | 0.1 |
| Monoethanolamine | q.s. | q.s. | q.s. |
| Purified water | q.s. | q.s. | q.s. |
| pH | | 9-10 | |
| Total | 100 | 100 | 100 |
| Mass ratio (A/B) of the content of component (A) to the content of component (B) | — | — | 1.667 |
| Rating | | | |
| Color in hair dyeing | 2 | 1 | 2 |
| Color after fading | 3 | 1 | 2 |

As shown in Table 1, it was confirmed that the hair dye composition of each Example containing (A) HC BLUE No. 2, (B) DISPERSE VIOLET 1, and (C) HC YELLOW No. 2 or HC YELLOW No. 4 and having a pH of 7 to 11 provided the results of a rating of 3 or more in each evaluation item. Particularly, it was confirmed that the hair dye compositions in Examples 5 to 20, in which the mass ratio of the content of (A) HC BLUE No. 2 to the content of (B) DISPERSE VIOLET 1 was 1 to 30 had a better color in hair dyeing than those in other Examples. It was also confirmed that the hair dye compositions in Examples 9 to 20, which further contained (D) DISPERSE BLACK 9, had a better color after fading than those in other Examples, which did not contain (D) DISPERSE BLACK 9.

Further, as shown in Table 2, it was confirmed that the hair dye composition in Comparative Example 1, which did not contain (A) HC BLUE No. 2, particularly had a low rating of the color in hair dyeing compared with those in each Example. It was confirmed that the hair dye composition in Comparative Example 2, which did not contain (B) DISPERSE VIOLET 1, had a low rating of the color in hair dyeing and the color after fading compared with those in each Example. It was confirmed that the hair dye composition in Comparative Example 3, which did not contain (C) HC YELLOW No. 2 or HC YELLOW No. 4, had a low rating of the color in hair dyeing and the color after fading compared with those in each Example.

The invention claimed is:

1. A hair dye composition consisting essentially of (A) HC BLUE No. 2 in an amount in a range of 0.1% to 3% by mass; (B) DISPERSE VIOLET 1 in an amount in a range of 0.05% to 1.5% by mass; (C) at least one of HC YELLOW No. 2 and HC YELLOW No. 4, in an amount in a range of 0.2% to 0.8% by mass; (D) DISPERSE BLACK 9 in an amount in a range from 0.05% to 0.5% by mass, and an organic solvent, wherein the composition has a pH of 7 to 11, the composition is constituted as a one-pack type composition in which all components constituting the hair dye composition are blended in, and the composition is a semi-permanent hair dye.

2. The hair dye composition according to claim 1, wherein the mass ratio of the content of (A) HC BLUE No. 2 to the content of (B) DISPERSE VIOLET 1 is 1 to 30.

3. The hair dye composition according to claim 1, wherein the composition is used for dyeing hair in brown to black color.

* * * * *